(12) United States Patent
Kanno

(10) Patent No.: US 7,214,767 B2
(45) Date of Patent: May 8, 2007

(54) VHL PEPTIDE

(75) Inventor: Hiroshi Kanno, Kanagawa (JP)

(73) Assignees: Hiroshi Kanno, Kanagawa (JP); Toagosei Co., Ltd., Tokyo (JP)

( * ) Notice: Subject to any disclaimer, the term of this patent is extended or adjusted under 35 U.S.C. 154(b) by 0 days.

(21) Appl. No.: 11/136,429

(22) Filed: May 25, 2005

(65) Prior Publication Data

US 2006/0270834 A1   Nov. 30, 2006

(51) Int. Cl.
   *C07K 5/00*   (2006.01)

(52) U.S. Cl. ..................................... 530/300

(58) Field of Classification Search ............... None
   See application file for complete search history.

(56) References Cited

U.S. PATENT DOCUMENTS 6,084,068 A * 7/2000 Conaway et al. ........... 530/350

FOREIGN PATENT DOCUMENTS

| WO | 00/69908 | 11/2000 |
| WO | WO0191798 | * 12/2001 |
| WO | WO03064609 A2 | * 8/2003 |

OTHER PUBLICATIONS

Fuchs et al. Cell 2000. 100: 143-155.*
H. Kanno et al., "Role of the von Hippel-Lindau Tumor Suppressor Protein during Neuronal Differentiation", *Cancer Research*, vol. 60, pp. 2820-2824, 2000.
F. Latif et al., "Identification of the von Hippel-Lindau Disease Tumor Suppressor Gene", *Science*, vol. 260, pp. 1317-1320, 1993.
J. Gnarra et al., "Molecular Cloning of the von Hippel-Lindau Tumor Suppressor Gene and Its Role in Renal Carcinoma", *Biochemical et Biophysica Acta*, vol. 1242, No. 3, pp. 201-210, 1996.
D. Watkins et al., "Genetics, Prognosis and Therapy of Central Nervous System Tumors", *Cancer Detection and Prevention*, vol. 18, No. 2, pp. 139-144, 1994.
J. McDonald et al., "Transplanted Embryonic Stem Cells Survive, Differentiate and Promote Recovery in Injured Rat Spinal Cord", *Nature Medicine*, vol. 5, No. 12, pp. 1410-1412, 1999.
Fisher, "Neural Precursor Cells: Applications for the Study and Repair of the Central Nervous Sysytem," *Neurobiology of Disease*, vol. 4, pp. 1-22, 1997.
Murray et al., "Transgenic Animals in Agriculture", *CAB International: Oxon*, pp. 59-60, 1999.

(Continued)

*Primary Examiner*—Janet L. Andres
*Assistant Examiner*—Chang-Yu Wang
(74) *Attorney, Agent, or Firm*—Wenderoth, Lind & Ponack, L.L.P.

(57) ABSTRACT

Intractable neuronal diseases are treated by inducing differentiation of neural stem cells into neurons without accompanying a risk such as cytotoxicity and infection. Intractable neuronal diseases, such as Parkinson's disease, cerebral infarction, Alzheimer's disease, spinal cord injury, brain contusion, amyotropic lateral sclerosis, Huntington's disease, malignant tumor, and the like, are treated by regeneration therapy by transferring VHL peptides which can induce differentiation of neural stem cell into neurons into neural stem cells to induce differentiation of neural stem cells into neurons or by administering VHL peptides directly into a human body to induce differentiation of endogenous stem cells into neurons.

3 Claims, 7 Drawing Sheets
(6 of 7 Drawing Sheet(s) Filed in Color)

OTHER PUBLICATIONS

Isacson et al., "Benefits and risks of hosting animal cells in the human brain," *Nature Medicine*, vol. 3, No. 9, pp. 964-969, 1997.

Kanno et al., "Regulation of Differentiation by VHL Gene in Neural Stem Cells and Cell Death", *Neuroimmunological Research*, vol. 13, pp. 85-90, 2003 (including English Abstract).

Ohh et al., "Synthetic peptides define critical contacts between elongin C, elongin B, and the von Hippel-Lindau protein", *The Journal of Clinical Investigation*, vol. 104, No. 11, pp. 1583-1591, 1999 (including English translation).

Asao, "Elongin BC complex that controls multiple intracellular functions", *Biochemistry*, vol. 71, No. 4, pp. 279-282, 1999.

Tanaka, "The role of von Hippel-Lindau protein in the differentiation of neural progenitor cells under normoxic and anoxic conditions", *Neuroscience Letter*, vol. 383, pp. 28-32, 2005.

Yamada et al., "Transfer of the von Hippel-Lindau Gene to Neuronal Progenitor Cells in Treatment for Parkinson's Disease", *Ann. Neurol.*, vol. 54, pp. 352-359, 2003.

* cited by examiner

Induction of VHL Peptide (157-171) Using BIO PORTER KIT
(After 24 hours)

Marker of Neuron (72%)   Marker of Neuroglia Cell (12%)

Apomorphine Induced Rotation for 6-Hydrodopamine Parkinson's Disease Model Rat

VHL PEPTIDE

TECHNICAL FIELD

The present invention relates to oligopeptides having a partial amino acid sequence of von Hippel-Lindau (VHL) protein which can induce neuronal differentiation of stem cells (hereinafter referred to as "VHL peptide"). Stem cells into which VHL peptides of the present invention are introduced can induce neuronal differentiation. Neurons which are induced to differentiate are taken either by grafting to the central nervous system or peripheral nerves and then allowing to be functioned as neurons or by directly administering to a human body and then allowing endogeneous stem cells to differentiate into neurons thereby making it possible to treat Parkinson's disease, cerebral infarction, Alzheimer's disease, spinal cord injury, brain contusion, amyotropic lateral sclerosis, Huntington's disease or malignant tumor.

BACKGROUND ART

A neuron is a main element controlling the life activity of an individual higher organism. It had been thought that neurons of the certain nervous system perform neither postnatal differentiation nor regeneration, but only deciduate from one minute to the next. However in the 1990s, neural stem cells which had not yet differentiated into neurons were first found in a fetal brain, and as a result of further demonstration of the presence of neural stem cells in an adult brain, a possibility of regeneration of the central nervous system has been shown. Thus, a possible therapy for intractable neuronal diseases using tissue stem cells such as neural stem cells, and embryonic stem cells (ES cells) are in the limelight. However, there are problems that somatic stem cell such as neural stem cell as well as embryonic stem cell, even when it is transplanted as it is, does not differentiate into neuronal cell (neuron) and has a difficulty even in taking, and that most of them, even when taken, differentiate into glial cells. In addition, neuronal cells (neuron) which are easiest to induce differentiation into neural stem cells are difficult to collect from the brain of the same individual, and when human fetal brain is used, problems associated with ethical issues and rejection reaction must be overcome. In the case of bone marrow interstitial cells, skin stem cells and adipose stem cells, which are reported to differentiate into other neuronal cells, they are difficult to induce neuronal differentiation, and thus a technique for induction to neuron at a high yield for a short period of time has not yet been established.

Regarding these problems, we have considered that VHL gene and VHL protein may play a role from the developmental stage of neurons based on the fact that they are specifically expressed in neurons of the central nervous system, and then we have studied the expression of VHL protein in neural stem cells. Since VHL protein is expressed mainly in the cytoplasm as neural stem cells differentiate into neurons, and further, introduction of VHL gene into neural stem cells using a viral vector promotes differentiation into neurons while neuronal stem sell as it is inhibits inversely differentiation into neuron by inhibiting the action of VHL gene using antisense oligonucleotide which is an inverse sequence of messenger ribonucleic acid (RNA) of VHL gene, it has now been clarified that VHL gene has an ability to induce neuronal differentiation (non patent literature 1). It is affirmed that this ability of VHL gene to induce neuronal differentiation is a common phenomenon in neuroblastoma (non patent literature 2), ES cell, skin stem cell and bone marrow stromal cell. Nurr 1 and Mash 1 are known to be a gene showing an ability to induce neuronal differentiation like VHL gene, but only a method of gene transfer into a cell by using some vector has been reported until now. Thus, any trial to induce neuronal differentiation by introducing into a stem cell a protein having a powerful ability to induce neuronal differentiation instead of the gene has not yet been made. Furthermore, a method of activating an endogeneous neural stem cell and promoting regeneration of nerve by introducing into a body a protein having an ability to induce neural differentiation has not yet been developed. The preparation of a chemically synthesizable oligopeptides showing an ability to induce neuronal differentiation has not been reported. In addition, the utilization of such oligopeptides for regeneration of nerve has also not been reported.

In the United States, clinical trials using fetal brain obtained by artificial termination of pregnancy for treating Parkinson's disease have been already conducted and a certain effect has been recognized. At the level of animal experiment, a trial, in which neural stem cells or ES cells are grafted to the brain or spinal cord, and the cells are allowed to differentiate into neurons. has been started to treat intractable neuronal diseases including not only Parkinson's disease but also brain infarction, spinal cord injury and the like. Moreover, regeneration of peripheral nerve in vitro or in vivo in the form of bundles of nerve fibers has already been attempted. However, since neurons do not principally divide and proliferate, it is difficult to form practical bundles of nerve. In nerve grafting to treat ruptured peripheral nerve, normally the autologous nerve of a lower limb is excised and grafted. However, production of artificial nerve for nerve grafting in place of autologous nerve has not been successful.

[non patent literature 1] Kanno H et al.: Cancer Res 60: 2820–4, 2000

[non patent literature 2] Murata H, et al.: Cancer Res 62: 7004–7011, 2002

DISCLOSURE OF THE INVENTION

PROBLEMS TO BE SOLVED BY THE INVENTION

The problem to be solved is that introduction of VHL gene showing an ability to induce neuronal differentiation for the promotion of differentiation of neural stem cell into neuron is accompanied by many risks.

MEANS TO SOLVE THE PROBLEMS

The present invention is characterized by treating intractable neuronal diseases such as Parkinson's disease, cerebral infarction, Alzheimer's disease, spinal cord injury, brain contusion, amyotropic lateral sclerosis, Huntington's disease or malignant tumor by regeneration therapy comprising introducing into neural stem cell VHL peptide capable of inducing differentiation of neural stem cell into neuron or administering VHL peptide directly into a human body to induce differentiation of endogeneous stem cell into neuron.

EFFECTS OF THE INVENTION

The introduction of VHL peptide of the present invention not relying upon the gene transfer makes possible neuronal differentiation of somatic stem cells. Little cytotoxicity is found in fusion of VHL peptide to TAT (amino acid sequence of SEQ ID NO: 2: YGRKKPRQRRRD) or ANT (amino acid sequence of SEQ ID NO: 3: KKWKMRRN-QFWVKVQRGK) which facilitates the penetration of cell membrane. Furthermore, peptide introduction has no risk associated with infection which is found in viral vectors. Therefore, synthesized peptides have an advantage that they can be used in a manner similar to normal drugs.

BRIEF EXPLANATION OF FIGURES

The patent or application file contains at least one drawing executed in color. Copies of this patent or patent application publication with color drawings will be provided by the Office upon request and payment of the necessary fee.

BEST MODE FOR CARRYING OUT THE INVENTION

The present invention encompasses the following inventions:
(1) VHL peptide containing a partial amino acid sequence of von Hippel-Lindau protein inducing differentiation of stem cells into neuron.
(2) VHL peptide described in (1) containing 15 amino acids of from 157 position to 171 position of the amino acid sequence of von Hippel-Lindau protein.
(3) VHL peptide described in (2) which is an amino acid sequence of SEQ ID NO: 1 (TLKERCLQVVRSLVK).
(4) VHL peptide described in (3) wherein its N-terminal or C-terminal is fused to TAT of the amino acid sequence of SEQ ID NO: 2 or ANT of the amino acid sequence of SEQ ID NO: 3.
(5) VHL peptide described in any one of (1) to (4), which is transferred to a stem cell.
(6) VHL peptide described in (1) wherein the stem cell is selected from the group consisting of neural stem cell, skin stem cell, bone marrow stromal cells, adipose stem cell and embryonic stem cells.
(7) Neurons having the following properties, which are induced to differentiate from neural stem cell into which VHL peptide described in any one of (1) to (4) is introduced.
   (a) They express neurofilament and microtubule associated protein 2 as neuron specific protein.
   (b) They can transmit electric signals as a nerve to form a neural circuit.
   (c) They can take and function as neuron to be used for the treatment of diseases associated with neuronal function having disorder, when they are grafted to the central nervous system or peripheral nervous system after in vitro culturing and proliferation.
(8) Neurons described in (7) wherein the stem cell is selected from the group consisting of neural stem cell, skin stem cell, bone marrow stromal cells, adipose stem cell and embryonic stem cells.
(9) Neurons described in (7) wherein the disease is selected from the group consisting of Parkinson's disease, cerebral infarction, Alzheimer's disease, spinal cord injury, brain contusion, amyotropic lateral sclerosis, Huntington's disease and malignant tumor.

The present invention is explained below in more detail.

Figure 1:
FIG. 1 is a fluorescence photomicrograph showing induction of differentiation of skin stem cell into neurofilament positive neuron.

A VHL gene, which is the causative gene of von Hippel-Lindau disease, a hereditary disease causing brain tumor (hemangioblastoma) or renal cancer, is a kind of a tumor suppressor gene. This gene was isolated from human chromosome 3 by Dr. Zbar et al.'s group (U.S.A.) in 1993. It has been reported that the VHL gene and the protein are expressed in neurons. However, the function of this gene in the nervous system was unknown. We considered that the gene may be involved in the formation of the nervous system at fetal developmental stages and studied differentiation over time of neural stem cells isolated from a rat fetal brain. Thus, we have found that VHL proteins are expressed in neurons as neural stem cells differentiate into neurons. As it was suggested from the above that VHL protein is involved in differentiation of neurons, we have introduced VHL gene into neural stem cells using a herpes simplex vector and then we have studied whether the expression of VHL protein differentiates to neurons. As a result, when VHL gene is introduced to express VHL protein, neural stem cells are differentiated into neurons. Thus, it was clarified that VHL protein has a function to induce differentiation of nerves. Conversely, it was shown that inhibition of the functions of VHL gene in neural stem cells by a reverse sequence of messenger RNA of VHL gene (antisense) does not differentiate neural stem cells into neurons, and that neural stem cells hold by the inhibition of differentiation (the above non patent literature 1). It was proved that this function of VHL protein is shown not only for neural stem cells but also for neuroblastoma which is a kind of cancer cells, and that the introduction of VHL gene into neuroblastoma differentiates neuroblastoma into functional neurons (the above non patent literature 2). Furthermore, it was proved that VHL protein induces differentiation of skin stem cells into neurons (FIG. 1).

According to the present invention, VHL protein is not expressed in cells into which VHL gene was introduced, but neuronal differentiation is induced by introduction of VHL protein itself into somatic stem cell such as neural stem cell, and embryonic stem cell (ES cell). VHL protein is a relatively small protein consisting of 213 full length amino acids, and it is advantageous to introduce smaller protein into cells and it is also easy to synthesize a smaller one. An amino acid sequence of 15 amino acids (VHL 157–171) which is a site binding to elongin B and C, and selected from two sites binding to a ligand of VHL protein (binding protein) is determined to be a site showing the most important function involved in the function of neuronal differentiation as a part having a function inducing neuronal differentiation among the full length VHL protein in view of the three dimensional structure of VHL protein.

EXAMPLE 1

Figure 2:
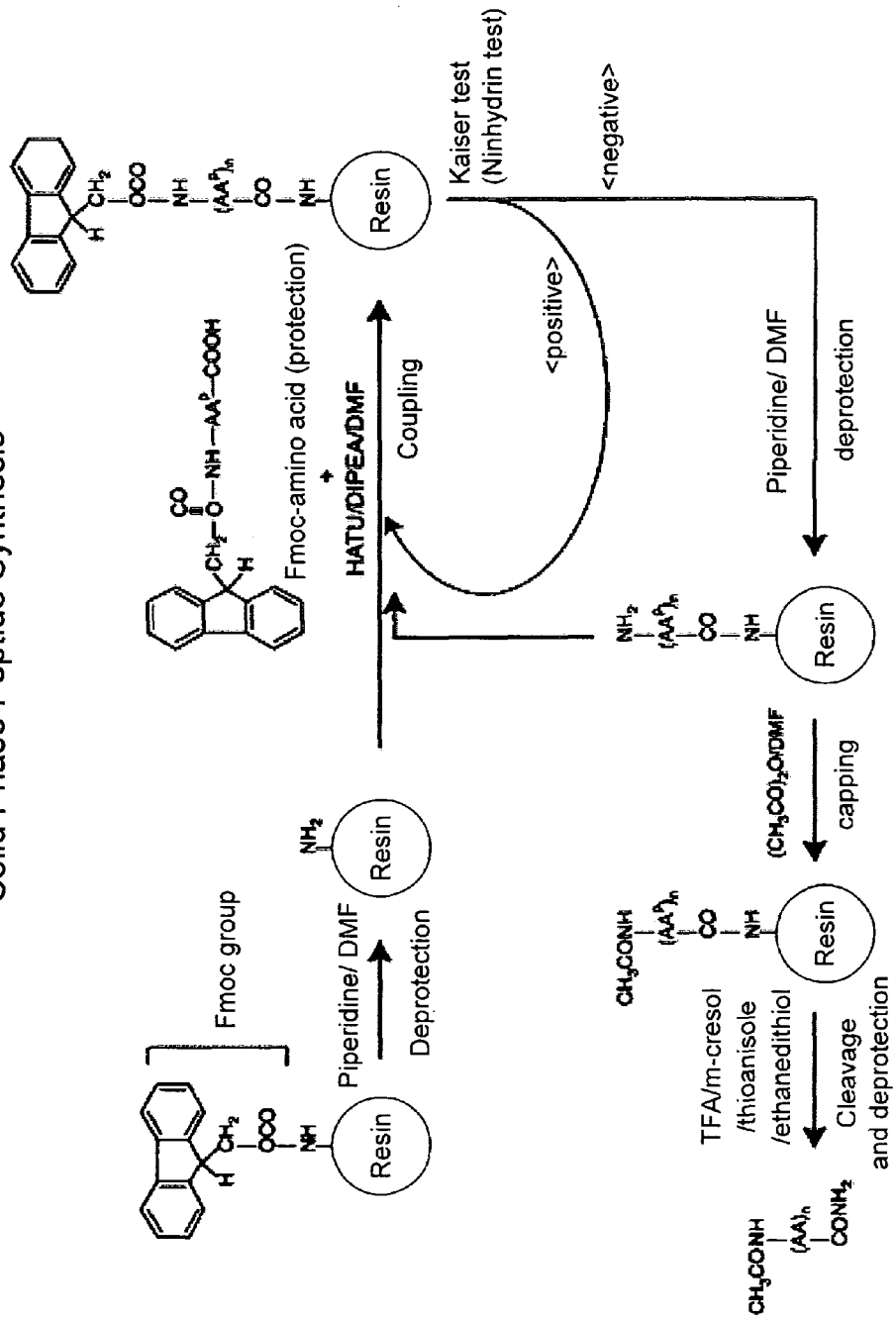
FIG. 2 explains the synthesis of the peptides of the present invention according to solid phase peptide synthesis method.

VHL oligopeptide of amino acids No. 157 to No. 171, which is a binding site of elongin, that is an important binding protein of VHL protein. was prepared according to solid phase synthesis method based on Fmoc method. Solid phase synthesis of an oligopeptide based on Fmoc method was performed. Fmoc-SAL-PEG resin (Watanabe Chemical) was used as solid carrier. By using this resin, an oligopeptide carboxyl(C) terminal of which is aminated can be obtained. After this resin was washed with DMF (N,N-dimethylformamide), Fmoc which is a protective group of amino group was removed with 20% piperidine/DMF. After wash with DMF, condensation reaction of amino acids was carried out by adding 3 equivalents of Fmoc-AA (amino acid)-OH/3 equivalents of HATU (O-(7-azabenzotriazole-1yl)-1,1,3,3-tetramethyluronium-hexafluorophosphate)/6 equivalents of DIEA (diisopropylethylamine) for the amino group on the resin, and the progress of the condensation reaction was confirmed by ninhydrin reaction. After the completion of coupling of all of the amino acids. Fmoc group was removed by 20% piperidine/DMF and then amino (N) terminal was acetylated with acetic anhydride. The resin the preparation of which was completed was dried in vacuum and m-cresol/ethaneditiol/thioanisole/TFA (trifluroroacetic acid) were added. Removal of the oligopeptide from the resin and the deprotection of amino acid side chain (p) were carried out by stirring one hour at room temperature (FIG. 2). This filtrate was ether precipitated to obtain a crude peptide. The crude peptide was purified by reverse phase HPLC to obtain the desired oligopeptide. The molecular weight of the synthesized peptide was confirmed by MADLI-TOF type mass spectroscopy and the concentration of the peptide was calculated from absorbance index in UV region of aromatic amino acid residue.

Figure 3:
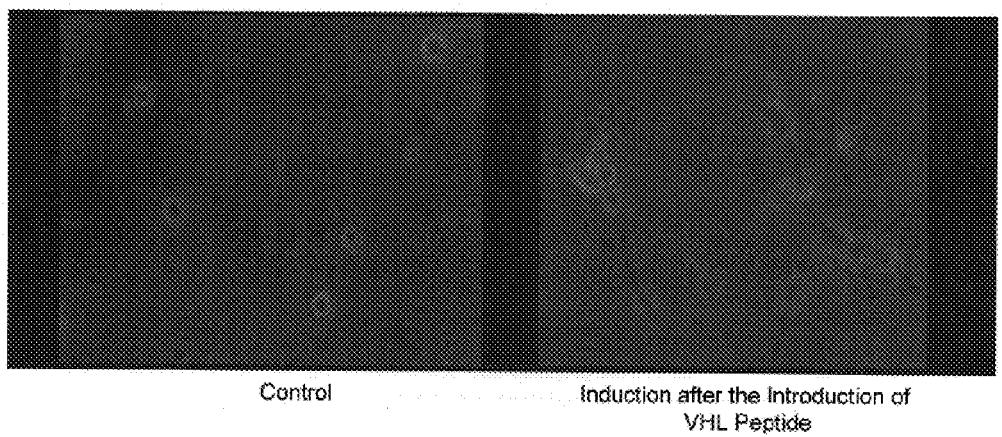
FIG. 3 is a fluorescence photomicrograph showing that when VHL peptide is introduced into neural stem cell using BioPORTER reagent, morphological change 8 hours after introduction is marked as compared with control group and neural stem cell tends to differentiate into neuron.
Figure 4:
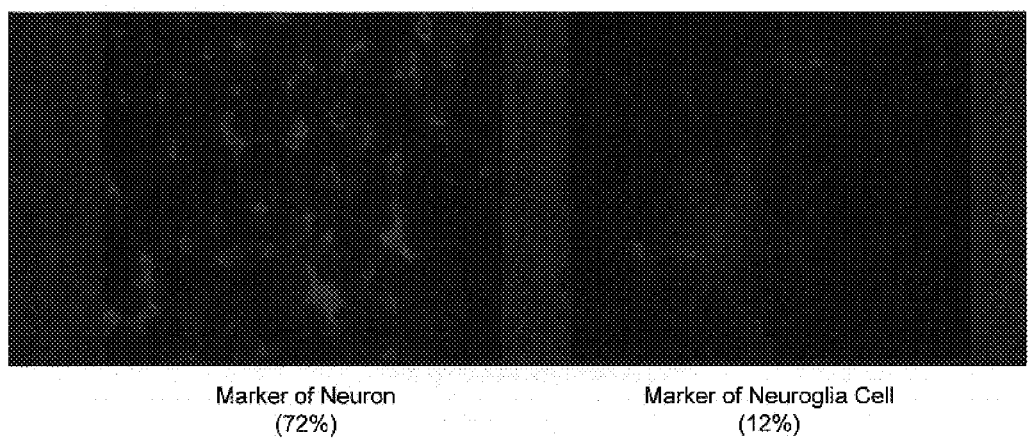
FIG. 4 is a fluorescence photomicrograph of immunoflurorescence stained cells showing that when VHL peptide is introduced into neural stem cells using BioPORTER reagent, 72% of it is differentiated into neuron and 12% of it is differentiated into neuroglia 24 hours after the introduction.

The oligopeptide prepared according to the above-described method was introduced in vitro into neural stem cells derived from the adult rat hippocampus at a concentration of 10–1000 ng/ml using BioPORTER Reagent (BioPORTER protein delivery reagent: Gene Therapy Systems, Inc., San Diego, Calif., U.S.A.). Thereby, neural stem cells showed inclination to differentiate to neuron morphologically at a concentration of not less than 10 ng/ml after 4 hours, and elongation of neural spine was observed. Eight hours after introduction, its morphological change was more marked as compared with the control group (FIG. 3). When this was immunofluorescence stained at a concentration of 100 ng/mL 24 hours after introduction, it was confirmed that 72% of them was differentiated into neurons, and 12% was differentiated into neuroglia cells (FIG. 4). Thereby, it was clarified that VHL could induce neuronal differentiation even by the method of peptide introduction not by introduction of gene.

Figure 5:
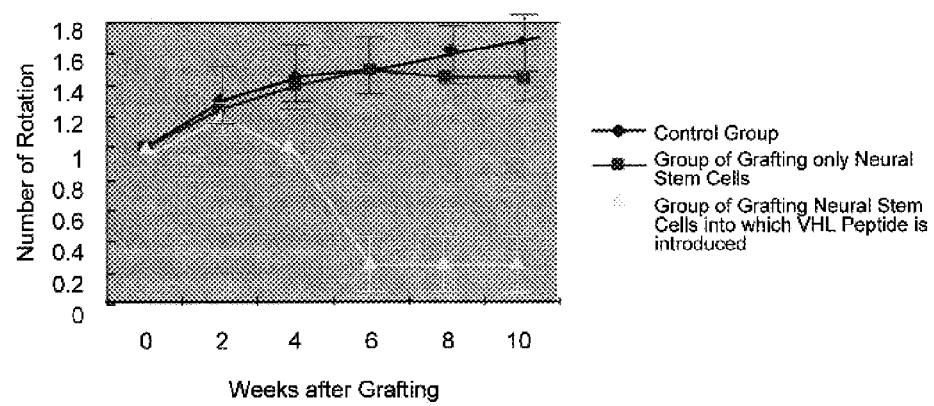
FIG. 5 shows the result of the determination of apomorphine induced rotation each week after grafting of VHL peptide transferred neural stem cells in the Parkinson model rat as neuronal disease animal which was prepared by injecting a small amount of 6-hydroxydopamine into the brain of rat, and in which unilateral dopamine producing cells were depleted. The results of only saline injection group as control group and grafting group of only neuronal stem cells are shown together.
Figure 6:
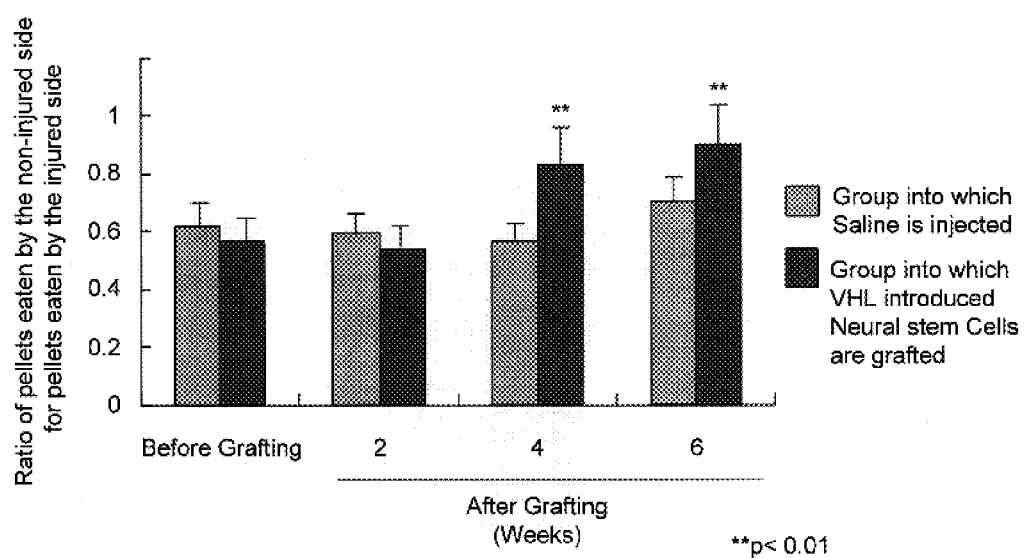
FIG. 6 shows the results of Paw reaching test for the above Parkinson model rat. Abscissa axis shows weeks after and before grafting of VHL peptide, and ordinate axis shows a ratio of pellets taken and eaten by the side of the injured leg. Neural stem cells grafted Parkinson model rat showed significant improvement in this behavior analysis as compared with control group.
Figure 7:
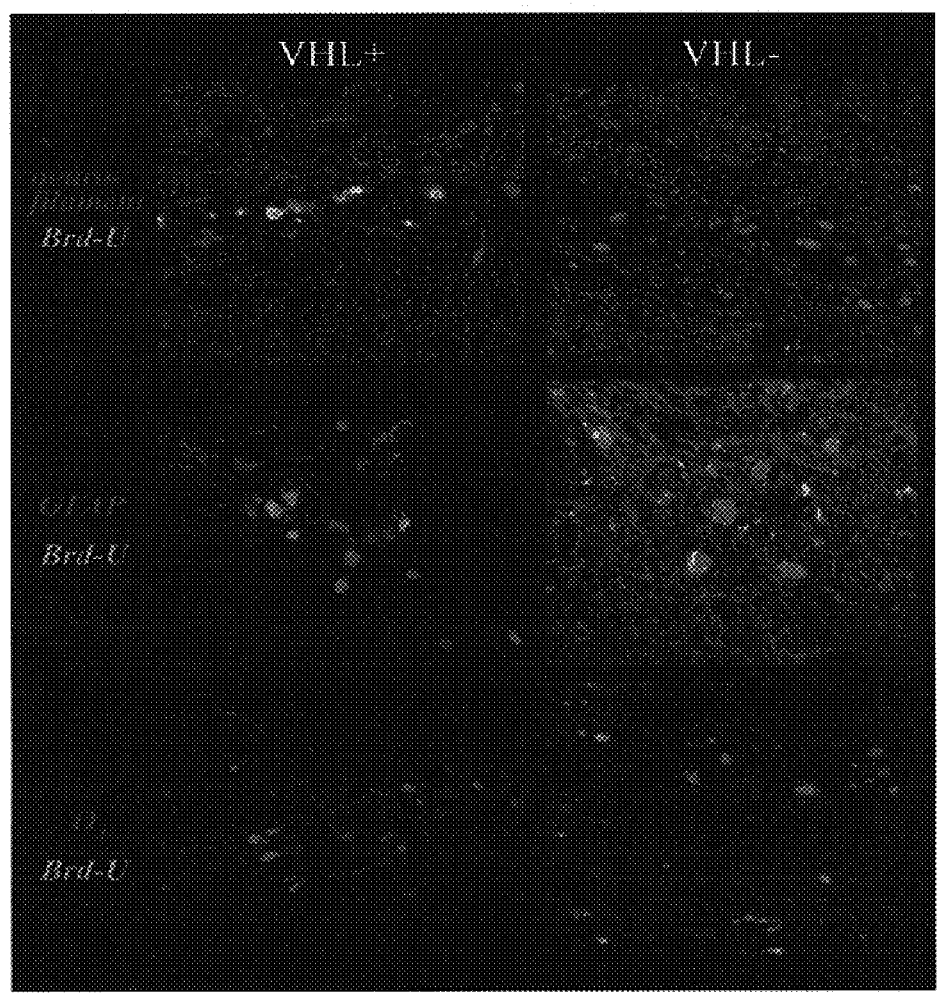
FIG. 7 is a microphotograph of tissues of the brain in the above Parkinson model rat into which VHL gene was grafted. It can be seen that about 70% of the grafted cells are taken within brain and most of them are neuronal filaments. In the figure, Brd-U shows bromodeoxyuridine. GFAP shows a marker of neuroglia, and O4 shows a marker of oligodendrocyte.

Next, it was studied whether the symptom could be improved by grafting of neural stem cells into which VHL (157–171) oligopeptide was introduced within the central nervous system of a nerve disease animal. Parkinson's model rat as a nerve disease animal was prepared by injection of microdose of 6-hydroxydopamine into brain of rat and depletion of unilateral dopamine producing cells. Two weeks later, apomorphine induced rotation was studied and rat rotating not less than 7 times per one minute was determined as Parkinson's disease model. $10^5$ neural stem cells into which VHL (157–171) oligopeptide was introduced were grafted to striatum of cerebrum of rat. After grafting, apomorphine induced rotation was determined every week. As a result, about 30% of rat showed zero of apomorphine induced rotation after two months (FIG. 5). As behavior analysis, paw reaching test (a test wherein an ability to eat pellets placed on stairs by extending one side injured leg is studied.) was conducted and VHL (157–171) oligopeptide was introduced (FIG. 6). Upon pathological and histological study of the brain of Parkinson's disease model rat into which VHL (157–171) ologopeptide introduced neural stem cells was grafted and which showed significant improvement in these behavior analysis as compared with the control group, about 70% of the grafted cells were taken within the brain and most of them were neurofilament positive neurons (FIG. 7).

Furthermore, a fusion protein which has an action of facilitating penetration through cell membrane was synthesized by binding TAT or ANT to VHL oligopeptide, and the resultant peptide in the form of TAT-VHL (157–171) or VHL (157–171)-ANT which was synthesized without using BioPORTER Reagent differentiated neural stem cells to neurons merely by adding it at a concentration of 10 ng/mL and introducing it into neural stem cells. It was thought that the method of binding a fusion protein penetrating through cell membranes was safer as compared to the method of using BioPorter Reagent, because it does not show cytotoxicity which BioPORTER Reagent has, and that the administration into a body was safe. Actually, when a fusion protein in which TAT was linked to an oligopeptide was administered into a body to make a therapeutic experiment, there was suggested a possibility that TAT-VHL (157–171) or VHL (157–171)-ANT could be used as medicine as it is. When this TAT-VHL (157–171) or VHL (157–171)-ANT was added into a culture medium of neural stem cells in vitro, it showed a physiological activity of inducing neuronal differentiation and thus it was proved that it is a functional peptide. When it was compared with TAT-VHL (104–121) showing tumor suppressing activity and merely TAT as a control group, TAT-VHL (157–171) showed the highest activity of inducing neuronal differentiation. It became clear from this that VHL (157–171) has an activity of inducing neuronal differentiation. Thus, it was found that TAT-VHL (157–171) was a functional peptide having a function of inducing neuronal differentiation.

Next, by varying a kind of cells, it was studied whether skin stem cell and bone marrow stromal cell among somatic stem cells have similar physiological activity. Skin stem cell was cultured after slicing dermis layer of skin of fetal rat and human into slices followed by passing through filter. The details of this culture method is described in Nature Cell Biology 2001 September; 3(9): 778–84. The culture medium was prepared by adding N2 supplement (Gibco), 10 ng/mL of basic fibroblast growth factor and 20 mg/mL of epidermal growth factor to DMEM/F12 (Gibco). When TAT-VHL (157–171) peptide was added to cells ten days after primary culture at a concentration of 100 ng/mL, differentiation to neurons was found 8 hours after the addition and it was clearly found 24 hours after the addition. As to bone marrow stromal cells, bone marrow cells are first separated from bone marrow of femora of 6 week old rat and then cultured in a culture medium of 10% FCS in RPMI. After subculture of two generation or three generation, only adhesive cells were treated over night by adding β-mercaptoethanol and then treated with DMSO for three hours. Further, after treatment with β-mercaptoethanol and DMSO for three hours, TAT-VHL (157–171) peptide was added at a concentration of 100 ng/mL, and continued to culture in culture plate coated with lysine. Then, differentiation to neurons was found 8 hours later and clearly 24 hours later.

INDUSTRIAL APPICABILITY

The present invention makes neuronal differentiation of somatic stem cells possible by introduction of peptide (protein) without reliance upon gene introduction. The present technique of gene introduction is accompanied by various dangers. When viral vectors are used, viral infection and cytotoxicity must be considered. In the case of plasmid vectors, efficiency of gene transfer is low, and cytotoxicity must be considered depending upon the method of transfer. On the contrary, little cytotoxicity was found in the linkage of a fusion protein making penetration through cell membrane possible using TAT or ANT. In addition, peptides (proteins) transfer do not have risk accompanied by infection which can be seen in viral vectors. Accordingly, the synthesized peptides (proteins) of the present invention can be used in a manner similar to the normal medicine. Accordingly, when the peptides of the present invention are considered as medicine, specific differentiation to neurons by administration becomes possible not only in vitro but also in vivo. By taking advantage of this, autologous tissues stem cells are taken out, and then differentiate to neural stem cells in vitro. Thereafter. nerves are regenerated by bringing back (self-grafting) to treat neuronal intractable disease such as Parkinson's disease, cerebral infarction, Alzheimer's disease, spinal cord injury. The present invention provides VHL peptide necessary therefor. Furthermore, it is possible to induce differentiation to neurons in vivo by administering VHL peptide having activity of inducing neuronal differentiation without taking out self endogenous neural stem cells. Thereby, nerves are regenerated and it is possible to treat intractable disease such as Parkinson's disease, cerebral infarction, Alzheimer's disease, spinal cord injury.

All of the publications, patents and patent application are incorporated into the present specification as it is as references.

The invention claimed is:

1. An isolated peptide consisting essentially of:
   (a) a 15 amino acid von Hippel-Lindau (VHL) peptide consisting of position 157 to position 171 of the amino acid sequence of the VHL protein; and
   (b) a TAT peptide having the amino acid sequence of SEQ ID NO: 2 or an ANT peptide having the amino acid sequence of SEQ ID NO: 3,
   wherein the TAT peptide or ANT peptide is fused to the C-terminal of the 15 amino acid VHL peptide.

2. The peptide of claim 1, wherein the 15 amino acid VHL peptide consists of the amino acid sequence of SEQ ID NO: 1.

3. The peptide of claim 1, wherein the ANT peptide is fused to C-terminal of the 15 amino acid VHL peptide.

* * * * *

```
                        SEQUENCE LISTING

<160> NUMBER OF SEQ ID NOS: 3

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Thr Leu Lys Glu Arg Cys Leu Gln Val Val Arg Ser Leu Val Lys
 1               5                  10                  15

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Tyr Gly Arg Lys Lys Arg Arg Gln Arg Arg Arg Asp
 1               5                  10

<210> SEQ ID NO 3
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Lys Trp Lys Met Arg Arg Asn Gln Phe Trp Val Lys Val Gln Arg
 1               5                  10                  15

Gly Lys
```